US008406373B2

(12) United States Patent
Graham et al.

(10) Patent No.: US 8,406,373 B2

(45) Date of Patent: Mar. 26, 2013

(54) OPTIMIZED APERTURE SELECTION IMAGING COMPUTED TOMOGRAPHY SYSTEM AND METHOD

(75) Inventors: Sean A. Graham, Etobicoke (CA); David A. Jaffray, Etobicoke (CA); Jeffrey H. Siewerdsen, Toronto (CA)

(73) Assignee: University Health Network, Toronto (CA)

(*) Notice: Subject to any disclaimer, the term of this patent is extended or adjusted under 35 U.S.C. 154(b) by 0 days.

(21) Appl. No.: 13/209,731

(22) Filed: Aug. 15, 2011

(65) Prior Publication Data

US 2012/0002781 A1 Jan. 5, 2012

Related U.S. Application Data

(63) Continuation of application No. 11/867,998, filed on Oct. 5, 2007, now abandoned.

(60) Provisional application No. 60/828,481, filed on Oct. 6, 2006.

(51) Int. Cl.
*A61B 6/03* (2006.01)

(52) U.S. Cl. ............... 378/16; 378/9; 378/153; 382/131

(58) Field of Classification Search .................. 378/2, 4, 378/65, 147–153, 9, 16; 250/505.1; 382/128–132
See application file for complete search history.

(56) References Cited

U.S. PATENT DOCUMENTS

| | | | | |
|---|---|---|---|---|
| 5,726,443 | A * | 3/1998 | Immega et al. | 250/227.2 |
| 6,052,430 | A * | 4/2000 | Siochi et al. | 378/65 |
| 6,920,203 | B2 * | 7/2005 | Short et al. | 378/147 |
| 6,999,556 | B2 * | 2/2006 | Nakano | 378/65 |
| 2005/0004446 | A1 * | 1/2005 | Cowan et al. | 600/407 |
| 2006/0193441 | A1 * | 8/2006 | Cadman | 378/153 |
| 2008/0152075 | A1 * | 6/2008 | Paliwal et al. | 378/16 |
| 2010/0119033 | A1 * | 5/2010 | Li et al. | 378/5 |

OTHER PUBLICATIONS

Graham et al., Intensity-Modulated Cone-Bean CT for Patient-Specific Distribution of SNR, Jul. 26, 2005, 47th Annual meeting of American Association of Physicists in Medicine, Abstract TU-D-I-661-4 and Power Point Presentation made on Jul. 26, 2005, 1 Page Abstract, 1 Page Program Announcement, 7 Pages of Power Point Presentation comprising 14 slid.*

Srinivas et al., Multiobjective Optimization Using Nondominated Sorting in Genetic Algorithms, 1995, Evolutionary Computation, vol. 2, No. 3, pp. 221-248.*

Wu et al., Fast Treatment plan modification with an over-relaxed Cimmino algorithm, 2004, Medical Physics, vol. 31, No. 2, pp. 191-200.*

Wu et al., Treatment plan modification using voxel-based weighting factors/dose prescription, 2003, Physics in Medicine and Biology, vol. 48, pp. 2479-2491.*

* cited by examiner

*Primary Examiner* — Toan Ton
*Assistant Examiner* — John Corbett
(74) *Attorney, Agent, or Firm* — Bereskin & Parr LLP/S.E.N.R.L., s.r.l.; Hubert Samuel Frost

(57) ABSTRACT

A method and imaging system for operating imaging computed tomography using a radiation source and a plurality of detectors to generate an image of an object. The method includes: defining a desired image characteristics; and performing calculations to determine the pattern of fluence to be applied by the radiation source, to generate said desired image quality or characteristics. Then, the radiation source is modulated, to generate the intended pattern of fluence between the beam source and the object to be imaged. The desired image characteristics can comprise at least one of desired levels of contrast-to-noise ratio (CNR) and signal-to-noise ratio (SNR), and may provide at least one of: desired image quality in at least one defined region of interest; and at least one desired distribution of said image quality.

15 Claims, 12 Drawing Sheets

OPTIMIZED APERTURE SELECTION IMAGING COMPUTED TOMOGRAPHY SYSTEM AND METHOD

CROSS REFERENCE TO RELATED APPLICATIONS

This application is a continuation of U.S. application Ser. No. 11/867,998 filed Oct. 5, 2007, which claims the benefit of U.S. application No. 60/828,481 filed Oct. 6, 2006, each of which is hereby incorporated herein by reference in its entirety.

FIELD

This specification relates generally to the field of computed tomography (CT) and more particularly to an optimized aperture selection imaging CT (OASCT) system and method utilizing compensating filters to modulate the fluence pattern applied during image acquisition for specific distributions of dose and image noise.

BACKGROUND

The following paragraphs are not an admission that anything discussed in them is prior art or part of the knowledge of persons skilled in the art.

Current imaging practice attempts to acquire high image quality throughout a scanned volume, though some focus is now being directed at more patient specific methods of imaging. It is recognized that many imaging tasks only require elevated image quality in smaller volumes while low image quality would be sufficient throughout the remainder of the imaged volume. The development of techniques to perform region of interest (ROI) imaging (see R. Chityala, K. R. Hoffmann, S. Rudin, and D. R. Bednarek, "Region of interest (ROI) computed tomography (CT): Comparison with full field of view (FFOV) and truncated CT for a human head phantom," Proc. *SPIE Physics of Medical Imaging* 5745, 583-590 (2005) and C. J. Moore, T. E. Marchant, and A. M. Amer, "Cone beam CT with zonal filters for simultaneous dose reduction, improved target contrast and automated set-up in radiotherapy," *Phys Med Biol* 51, 191-2204 (2006)) are a step towards acquiring images that provide varying image quality through the reconstructed volume. However, there remains a need for further improvements to be made by having the ability to optimally modulate the x-ray fluence patterns applied during imaging in a more patient specific fashion.

Many technologies have been developed for the purpose of improving external beam radiation therapy by imaging patients in the treatment position. These systems, which include CT imagers placed on rails in the treatment room (see K. Kuriyama, H. Onishi, N. Sano, et al. "A new irradiation unit constructed of self-moving gantry-CT and linac," *Int J Radiat Oncol Biol Phys* 55,428-35 (2003)), Tomotherapy (see T. R. Mackie, T. Holmes, S. Swerdloff, et al. "Tomotherapy: a new concept for the delivery of dynamic conformal radiotherapy." *Med Phys* 20, 1709-19 (1993)), and imaging CT systems mounted on the gantries of conventional linear accelerators have the potential to improve radiation therapy targeting. One example of a CT imaging system is cone-beam CT (see D. A. Jaffray, J. H. Siewerdsen, J. W. Wong, and A. A. Martinez, "Flat-panel cone-beam computed tomography for image-guided radiation therapy," *Int J Radiat Oncol Biol Phys* 53, 1337-1349 (2002)) and another example is scanning-beam CT (see E. G. Solomon, B. P. Wilfley, M. S. Van Lysel, A. W. Joseph, and J. A. Heanue, "Scanning-beam digital x-ray (SBDX) system for cardiac angiography," in *Medical Imaging* 1999: *Physics of Medical Imaging* (SPIE, New York, 1999), Vol. 3659, pp. 246-257; T. G. Schmidt, J Star-Lack, N. R. Bennett, S. R. Mazin, E. G. Solomon, R Fahrig, N. J, Pelc, "A prototype table-top inverse-geometry volumetric CT system." *Medical Physics*, June 2006 33(6), pp. 1867-78). With this improvement comes the possibility of reducing planned treatment volumes (PTVs), increasing the sparing of normal tissues and increasing the dose to tumors.

Also, a large quantity of work has been accomplished to improve the ability of systems designed for image guided radiation therapy to improve patient outcome. For the case of cone-beam CT, there is a large interest in developing flat-panel detectors with improved performance (dynamic range, spatial resolution) and removing the effects of scattered x-rays reaching the detector. It has now been shown that implementing compensating filters into imaging CT systems has the potential to play a large role in reducing scatter that reaches the detector, as well as scatter within the patient delivering unnecessary patient dose.

Accordingly, there is a need for an imaging system to optimize image quality in the most clinically relevant regions of an image, while reducing dose to the patient by reducing the fluence intensity outside defined regions of interests.

INTRODUCTION

The following introduction is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

In accordance with a first aspect of this specification, there is provided a method for operating imaging computed tomography using a radiation source and a plurality of detectors to generate an image of an object, the method comprising the steps of: (a) defining desired image characteristics; (b) performing calculations to determine the pattern of fluence to be applied by the radiation source, to generate said desired image characteristics; and (c) modulating the radiation source to generate said pattern of fluence between the beam source and the object to be imaged.

The present specification also provides an imaging system, the system comprising: (a) a radiation source for directing a beam at an object to be imaged; (b) a modulator placed between said beam source and the object to be imaged; and (c) a computer for performing calculations based on the desired distribution of image quality to determine the pattern of fluence to be applied by said temporal modulator.

The teachings of this specification can be applied to any suitable object. It is expected that it will be commonly used to examine a human or animal body.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIGS. 9*c* and 9*b* show, respectively, the SNR distribution and the image acquired with $W_{SNR}$ tripled in regions of higher SNR, using the SNR from FIG. 5*b*;

Figure 1:
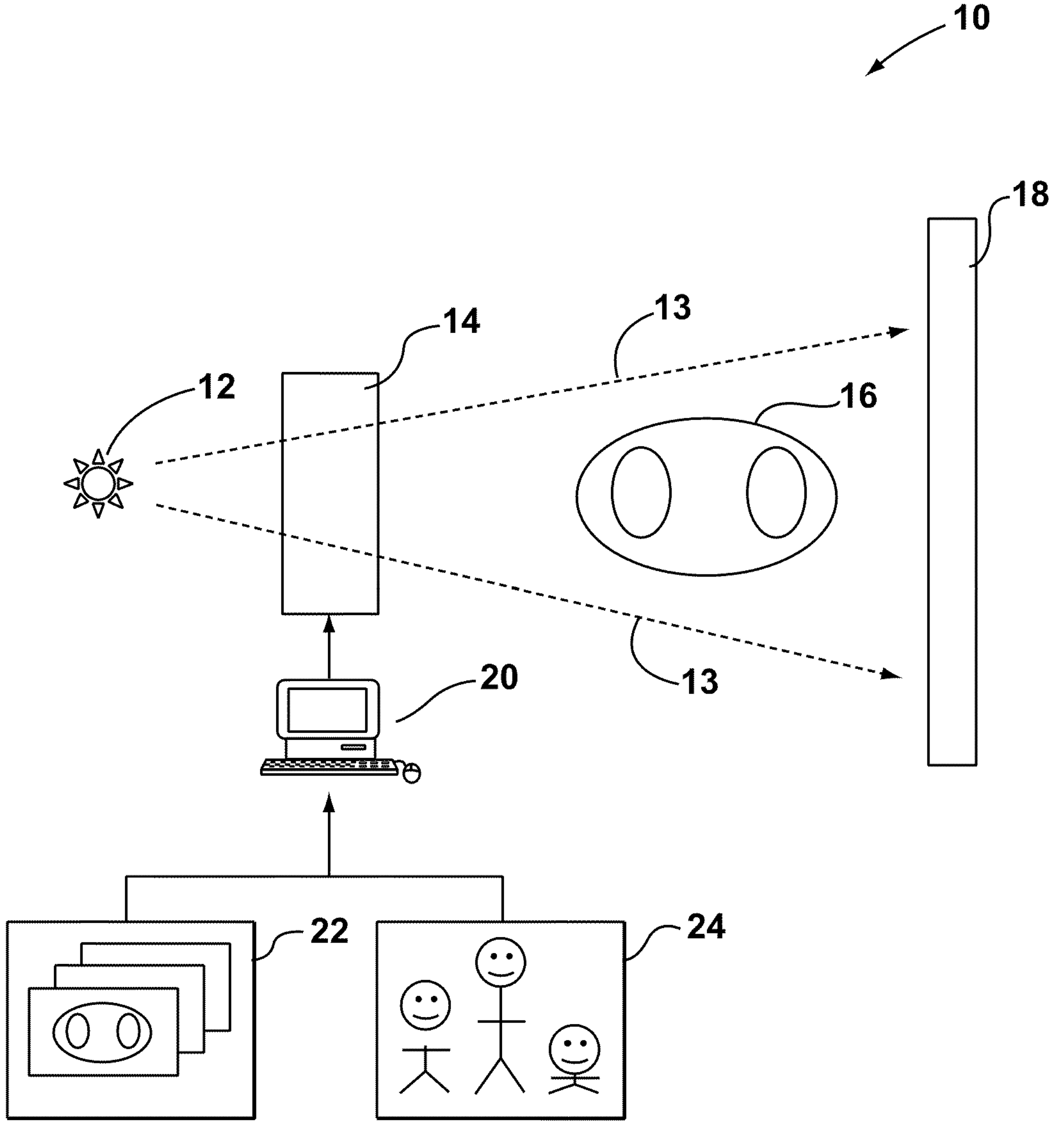
FIG. 1 is a block diagram of an example implementation of an imaging CT system.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

Various apparatuses or methods will be described below to provide an example of an embodiment of each claimed invention. No embodiment described below limits any claimed invention and any claimed invention may cover apparatuses or methods that are not described below. The claimed inventions are not limited to apparatuses or methods having all of the features of any one apparatus or method described below or to features common to multiple or all of the apparatuses described below. It is possible that an apparatus or method described below is not an embodiment of any claimed invention. The applicants, inventors and owners reserve all rights in any invention disclosed in an apparatus or method described below that is not claimed in this document and do not abandon, disclaim or dedicate to the public any such invention by its disclosure in this document.

The teachings of this specification have the potential to decrease dose to patients by concentrating image quality on desired regions of interest (ROIs) or distributions of image quality. An iterative optimization process is utilized to design patterns of modulation to be applied during imaging to acquire images as near as possible to those desired. This optimizing process can account for numerous parameters of the imaging CT system, including the efficiency of the detector, the presence of x-ray scatter reaching the detector, and the constraints of the modulator used to form the intensity modulated fluence patterns.

Reference is first made to FIG. 1, which illustrates an imaging CT system 10. Imaging CT system 10 can be any method of CT imaging, such as a cone-beam CT system or a scanning-beam CT system. It can also be an inverse-geometry volumetric system, as disclosed in the paper by T. G. Schmidt et al. noted above. Note that configurations of the present specification are not limited to x-ray sources or x-ray radiation and are applicable to other imaging systems, although the configuration of CT imaging systems, utilize an x-ray source and x-ray radiation.

Imaging CT system 10 comprises of an x-ray source 12, a modulator 14, an object to be imaged 16, an array of detectors 18, and a computer 20. Both x-ray source 12 and array of detectors 18 are placed on a rotational gantry (not shown) and are able to continuously rotate around the object to be imaged 16, so that the angle at which x-ray beam 13 intersects with the object to be imaged 16 constantly changes. The modulator 14 is a device placed between the x-ray source 12 and the object to be imaged 16 for effecting the desired fluence pattern as determined by computer 20. Detector array 18 is formed by a plurality of detector rows (not shown) including a plurality of detector elements (not shown) which together sense the radiation that passes through the object to be imaged 16. In operation, x-ray source 12 emits x-ray beams 13 through modulator 14 towards the object to be imaged 16 so that the array of detectors 18 can detect the x-ray fluence passing through the object to be imaged 16.

The resulting signals at the array of detectors 18 are then sampled by a data measurement system (not shown) to build up a projection, and subsequently a reconstructed volume. Note that the optimized aperture selection CT system and method can be implemented for any number of imaging geometries, source-detector trajectories, or reconstruction algorithms, such as cone-beam CT or scanning-beam CT.

Computer 20 is the computational engine of imaging CT system 10 which generates the operational parameters of modulator 14 to control the pattern of fluence to be applied during image acquisition based on a desired distribution of contrast-to-noise-ratio (CNR) (as will be discussed further below). Computer 20 makes use of either previously acquired patient images 22 to define regions of interest (ROIs) or a library of population models 24 to define a distribution of desired image quality.

Figure 2:
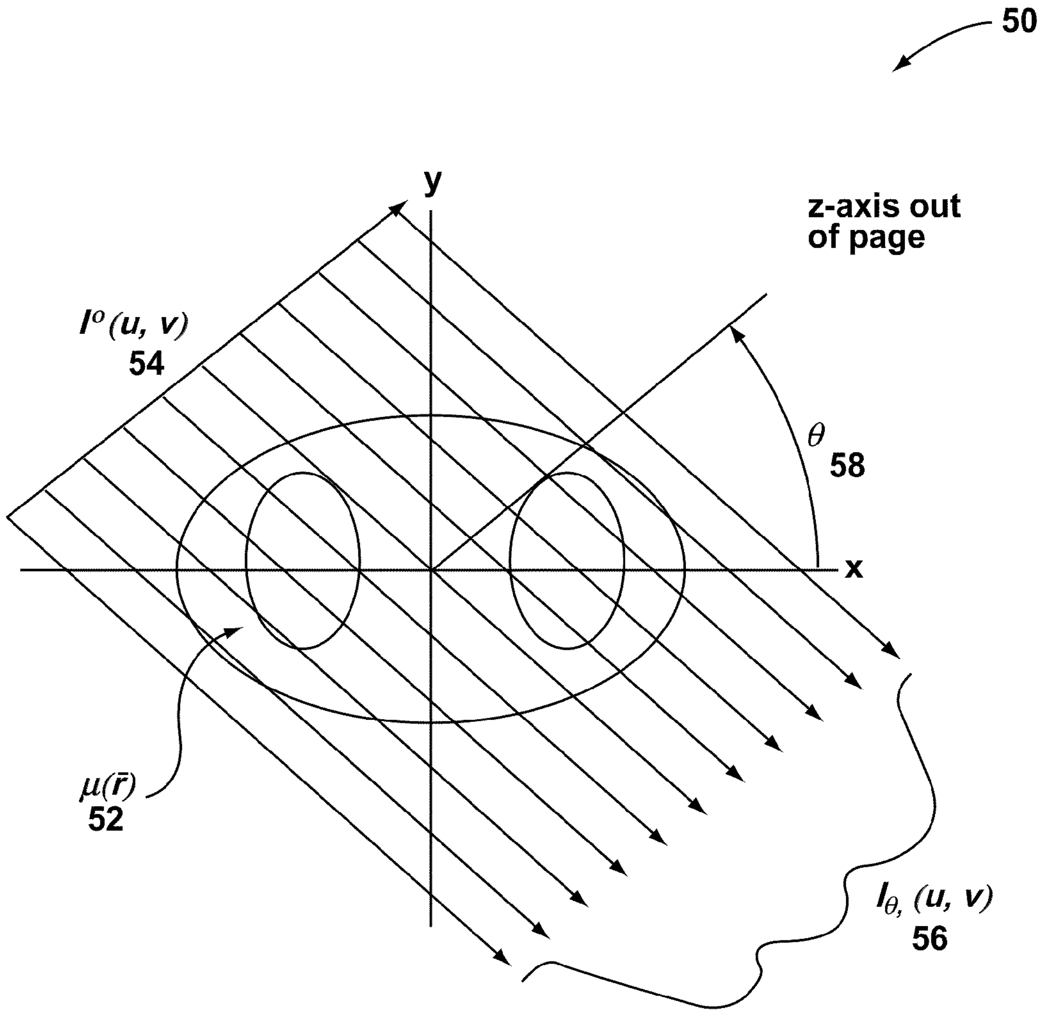
FIG. 2 is an illustrative block diagram of the imaging geometry being imaged by the imaging CT system of FIG. 1.
Figure 3:
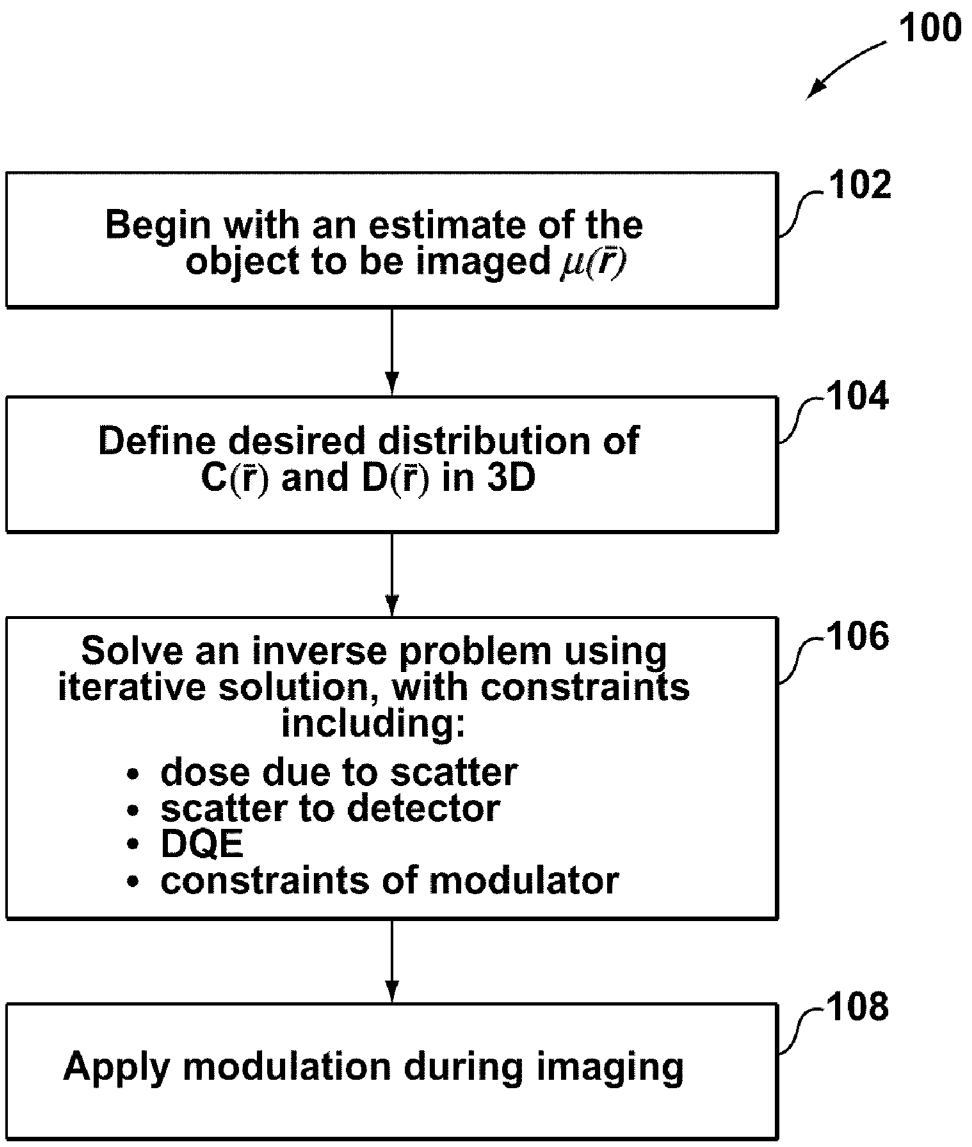
FIG. 3 is a flow chart illustrating the general process steps for optimal modulation determination.

Referring now to FIGS. 2 and 3, the general process steps 100 for determining optimized fluence patterns through modulation will be described for the imaging geometry 50 shown. Both the theory behind the design of imaging CT system 10 and its practical applications will be described in detail below.

At step 102, the process begins with an estimate of the object to be imaged 16 provided to computer 20. Object to be imaged 16 is described by attenuation function $\mu(\vec{r})$52 where $\vec{r}$ is the position of the voxels in the volume. Projection images of the object 52 are acquired by first directing a two-dimensional x-ray beam $I^O(u,v)$54 towards the object at each angle $\theta_i$ 58 to determine the detected x-ray fluence $I_{\theta_i}(u,v)$ 56 after passage through the object. The variables u and v represent the pixel matrix of the x-ray detector in use. In this work v=v(z) and u=u(x,y) where x, y, and z are the dimensions of the object being imaged. The x-y plane, or imaging plane, is the plane where the x-ray beam 54 projected by x-ray source is collimated to lie. The projections, without any modulation applied to the x-ray beam, are given by the following:

$$P_{\theta_i}(u,v)=-ln(I_{\theta_i}/I^O) \quad [1]$$

The detector has an exposure dependent detective quantum efficiency (DQE) given by the function $\phi(\theta,u,v)$,_where v=v(z) and u=u(x,y), and with x, y and z being the dimensions of the object being imaged.

In the present system and method, a modulation function $m_{\theta_i}(u,v)$ is introduced to provide modulated fluence patterns during imaging, and is effected in imaging CT system 10 through modulator 14. The modulation function, with values in the interval [0,1], describes the percentage of the incident two-dimensional x-ray beam 54 to be directed at the scanned object for each pixel (u,v) and each angle $\theta_i$ 58. Where the modulation factor is 1, this would be equivalent to imaging without any modulating filter placed in the beam.

Introduction of this modulation factor causes the x-ray fluence incident on the scanned object 54 to be $m_{\theta_i}(u,v)I^O(u,v)$, and the detected fluence through the object 56 to be $m_{\theta_i}(u,v)I_{\theta_i}(u,v)$. From these values the modulated projection images can be determined as:

$$P_{\theta_i}{}^m(u,v)=ln(m_{\theta_i}(u,v)I^O(u,v))-ln(m_{\theta_i}(u,v)I_{\theta_i}(u,v))=-ln(I_{\theta_i}/I^O) \quad [2]$$

and it is seen that imaging with modulated fluence patterns has no effect on the expected value of the projections for this idealized case.

The effect of the modulation is only seen when the noise in the projections is investigated. Assuming that the x-ray fluence is Poisson distributed, then the variance of the x-ray fluence through the object 52 will be given by the expected value of the fluence, $\bar{I}_{\theta_i}(u,v)$. For the modulated fluence patterns the variance will be $m_{\theta_i}(u,v)\bar{I}_{\theta_i}(u,v)$. This leads to variances in the projections of $$\text{var}\{P_{\theta_i}(u, v)\} = \frac{1}{\bar{I}_{\theta_i}(u, v)} \quad [3]$$

for the unmodulated case, and $$\text{var}\{P^m_{\theta_i}(u, v)\} = \frac{1}{m_{\theta_i}(u, v)\bar{I}_{\theta_i}(u, v)} \quad [4]$$

for the modulated fluence patterns. So, although the modulation function does not affect the expected value of the projections, it does affect the noise in the projections.

The projections can be used to form volumetric reconstructions. For a parallel beam geometry with no scatter or energy dependence the reconstructed image can be found with the formula $$f(x, y, z) = \frac{\pi\tau}{M_{proj}} \sum_{i=1}^{M_{proj}} \sum_k P^m_{\theta_i}(u, v)h(x\cos\theta_i + y\sin\theta_i - k\tau) \quad [5]$$

where $M_{proj}$ is the total number of projection images, T is the sampling interval of the object, and h is the inverse Fourier transform of the filtering function. The filtering of the projection takes place in the u(x,y) dimension of the projections, and is performed for each value of v(z). The expected value of the reconstruction is not affected by the modulation function, but the variance of the reconstructed image depends on the variance of the projections, given by the formula:

$$\text{var}\{f(x, y, z)\} = \left(\frac{\pi\tau}{M_{proj}}\right)^2 \sum_{i=1}^{M_{proj}} \sum_k \frac{1}{m_{\theta_i}(u, v)\bar{I}_{\theta_i}(u, v)} h^2(x\cos\theta_i + y\sin\theta_i - k\tau) \quad [6]$$

So it is evident that depending on the selection of the modulation function $m_{\theta_i}(u,v)$ there can be a variation in noise across a reconstructed volume. As such, an object of the present teachings is then to determine the modulation function that is optimal for a desired imaging task.

At step (104), the desired distribution can be defined. Given some metric $C(\vec{r})$ describing image characteristics (e.g. contrast-to-noise ratio (CNR) or signal-to-noise ratio (SNR) in a volumetric image, computer 20 determines a modulation function $m_{\theta_i}(u,v)$ which can be applied to x-ray intensities incident on the scanned object 52 to obtain an image which falls within a specified range from $C(\vec{r})$. An example of an image characteristic is the contrast-to-noise ratio (CNR), where the CNR distribution in the body for CT is dependent upon both the constraints of the object 52 and the fluence pattern applied 54 in the generation of the CT image, namely $CNRC(\vec{r})=f(\mu(\vec{r}), I_{\theta_i}(u,v))$. The CNR $(\vec{r})$ would be designed according to the object 52 and the anticipated location of the object 52 at the time of imaging.

The necessary modulation can be found by solving the inverse problem $$m(u,v)I(u,v)=G^{-1}[C(\vec{r})] \quad [7]$$

where $G^{-1}$ is an operator which relates the image metric $C(\vec{r})$ to the applied radiation intensities. This will result in a reconstructed image $\hat{f}(\vec{r})$ where $$\underline{C}(\vec{r})\leq\hat{f}(\vec{r})\leq\overline{C}(\vec{r}) \quad [8]$$

with $\underline{C}(\vec{r})$ and $\overline{C}(\vec{r})$ being the lower and upper bounds respectively desired of $C(\vec{r})$ at each point $\vec{r}$. This accounts for the fact that the desired $C(\vec{r})$ may not be obtainable with the possible modulation combinations. For example, if a matrix containing the desired image quality was 65×65 pixels, and 180 projections were desired, this would result in a modulation factor matrix of size 65×180 (a total of 11,700 values to be optimized). However, it is noted that one could cut the amount of processing required by using the symmetry of the desired image quality patterns optimized for the number of angles required to determine the modulation factor, reducing the problem to only 5,850 values.

An upper bound on $\overline{C}(\vec{r})$ is necessary to limit the dose applied during image acquisition, while the lower bound is necessary if sufficient image quality is to be obtained. Variable image quality can be defined in different regions of the image depending on the imaging task.

Careful characterization of the imaging CT system 10 is necessary to find the relationship between $m_{\theta_i}(u,v)$ and $C(\vec{r})$. In order to plan the fluence patterns that will lead to the desired image, it is necessary to take various quantities, that are also modulated by $m_{\theta_i}(u,v)$, into account such as: the dose in the scanned object where $D(\vec{r})=D(\mu(\vec{r}),I^O(u,v), m_{\theta_i}(u,v))$, the scattered radiation inherent to imaging CT systems $I_S(\mu(\vec{r}), I_O(u,v), m_{\theta_i}(u,v))$, and the exposure dependent detective quantum efficiency of the detector $DQE(v,\mu(\vec{r}),D/proj, I^O(u,v), m_{\theta_i}(u,v))$. The computational engine of computer 20 comprises a model for dependence of $CNR(\vec{r})$ and $D(\vec{r})$ on $I_{\theta_i}(u,v)$, including the above mentioned quantities.

It is not expected that it will be possible to determine an analytical solution to the inverse problem when taking account of the numerous dependencies. The constraints of the problem will be satisfied by computer 20 determining a numerical solution to the problem at step (106).

An iterative solution could have a form $$\min\{\|C(\vec{r})-C_i(\vec{r})\|\} \quad [9]$$

where with each step i the image metric $C_i(\vec{r})$ is calculated from the given properties of the imaging CT system 10 and compared to the desired quantity $C(\vec{r})$. Changes to the fluence modulating function $m_{\theta_i}(u,v)$ can be applied so that $C_i(\vec{r})$ approaches $C(\vec{r})$. For every iterative step this process will require determining the value of $C_i(\vec{r})$ given appropriate inputs. The determination of $C_i(\vec{r})$ can be accomplished by applying pre-determined look-up tables which contain information involved in the relationship between $m_{\theta_i}(u,v)$ and $C(\vec{r})$. With more flexibility available for the choice of $m_{\theta_i}(u,v)$ it becomes necessary to create more complicated look up tables.

Additionally it is possible to optimize multiple properties of the imaging CT system 10. For example, a modulation function could be found to achieve both an optimal image quality, $\|(C(\vec{r})-C_i(\vec{r})\|$ and an optimal patient dose, $\|D(\vec{r})-D_i(\vec{r})\|$, and an appropriate weighting could combine the two to determine the optimal modulation to apply to the fluence patterns, resulting in an iterative solution of the form $$\min\{\|C(\vec{r})-C_i(\vec{r})+w\|D(\vec{r})-D_i(\vec{r})\|\} \quad [10]$$

Another possible addition to this optimization would be to not only weight the relative importance of image quality and dose across the entire image, but to also weight the importance of dose and image quality in individual voxels. This would require a matrix of weights for image quality, $W_C(\vec{r})$, and for dose, $W_D(\vec{r})$, giving a final form for the iterative solution of $$\min\{\|W_C(\vec{r})(C(\vec{r})-C_i(\vec{r}))\|+w\|W_D(\vec{r})(D(\vec{r})-D_i(\vec{r}))\|\} \quad [11]$$

Although the parameters of x-ray scatter reaching the detector and the energy dependence of the x-rays used for imaging have been let out of the formulation discussed above, it should be apparent to one skilled in the art on how to modify the above formulas to account for these parameters.

In alternate embodiments, computer 20 of imaging CT system 10 could potentially use a small library of general modulation factors that are designed for certain anatomical regions. This would shorten the optimization process 100 as described above when performed for specific patients.

Finally, at step (108), once the proper modulation function is determined by computer 20 using the method described above, modulation can be applied during image acquisition. There are various possibilities for the construction of the modulator 14. A main consideration is whether to use a modulator 14 that operates with spatial modulation or temporal modulation.

A modulator 14 that spatially modulates would consist of a shaped material that uses differing thicknesses of the material to absorb differing percentages of the primary x-rays. One example of a simple spatially modulating filter is a Cu Compensator, where the modulator has a shape that is thicker for outer detector rows and thinner for inner detector rows. As a result of this shape the x-rays corresponding to the outer detector rows undergo greater filtering than the x-rays corresponding to the inner detector rows (see U.S. Pat. No. 6,647,095, Jiang Hsieh). For imaging CT system 10 the modulator 14 would ideally be able to have a different optimized shape for each angle that a projection image is acquired at. One of the potentially problematic aspects of the spatially modulated approach is the energy dependent absorption of the x-rays by the modulator 14. As has already been shown (see S. A. Graham, D. J. Moseley, J. H. Siewerdsen, and D. A. Jaffray, "Compensators for dose and scatter management in cone-beam CT" *Med Phys* (submitted)) spectral hardening from shaped filters placed in the beam can cause artifacts in reconstructed volumetric images. If this problem cannot be addressed it may be necessary to investigate alternate approaches.

Figure 10A:
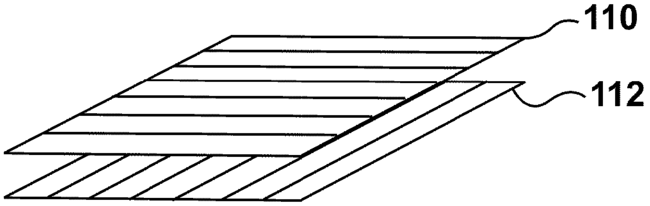
FIG. 10*a* shows a first embodiment of temporal compensation scheme, comprising a louvre compensator.

Temporal modulation is a possibility for avoiding problems associated with the energy dependent properties of the x-rays used for imaging. Rather than consisting of a material that partially absorbs incident x-rays a temporal modulator would be constructed of a material that absorbs most, if not all, of the incident photons. The modulation would be provided by having the modulator 14 block the x-rays for different amounts of time while moving across the projection image. FIG. 10 illustrates an embodiment of a temporal modulating filter, called a louvre compensator, where the material contains louvres that can be independently turned to create small field sizes during imaging. A combination of many of these small fields would provide the intensity-modulated pattern. FIG. 11 illustrates another embodiment, namely a multi-leaf compensator, where the material is made of small individual 'leaves' that slide across the field-of-view to create intensity modulated patterns. This approach would be similar to dynamic MLC IMRT (see P. Keall, Q. Wu, Y. Wu, and J. O. Kim, "Dynamic MLC IMRT," in *Intensity-modulated radiation therapy: The state of the art*. Edited by J. R. Palta and T. R. Mackie. Medical Physics Publishing, Madison, 2003), the contents of which are hereby incorporated by reference. It should be noted that both compensator examples could be constructed with any number of louvres or leaves depending on how coarse or fine a modulation pattern is desired. Although temporal modulation removes the complication of the energy dependent x-ray spectrum, there are other possible obstacles to be addressed. One possible issue is that the edges of the leaves in the modulator 14 may cause artifacts in the images that cannot be easily removed. There may also be difficulties in constructing a modulator 14 capable of moving the leaves with speeds high enough to modulate the fluence pattern during a projection, which takes place in a time on the order of 10 ms.

Demonstration of Optimized Aperture Selection Ct

Figure 4:
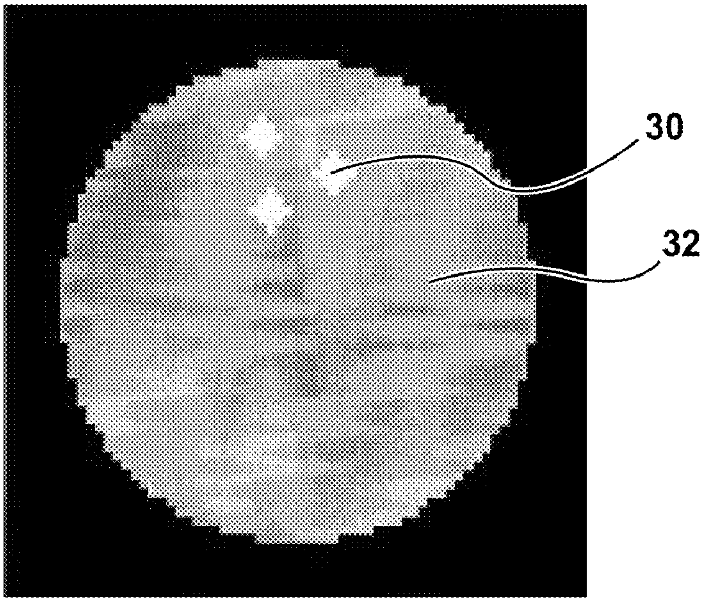
FIG. 4 shows a mathematical phantom used to model fluence patterns.

A demonstration of the ability to optimize fluence patterns to arrive at a desired image was performed in Matlab™. Optimized fluence patterns were determined for a circular mathematical phantom containing three simulated 'nodules' 30 of slightly different attenuation, in a body 32, as shown in FIG. 4. The optimization for determining the optimized fluence patterns was performed on a mathematical phantom without any simulation of surrounding soft tissue structure. This was done because when using this technique on patients we would not know the exact location of all soft tissue structures. It was decided that the optimization should be performed on a uniform object to avoid the changes in SNR that would be introduced by the change in attenuation. If the imaged area was to include regions with large variation in attenuation (i.e. bone or lung tissue) it is expected that these tissues would need to be included in the optimization.

The optimization routines available in Matlab were not able to manage the large number of variables to be optimized, requiring an alternative method to be used. A simple simulated annealing code was written to find modulated fluence patterns that provided low values of the cost function being minimized. The simulated annealing algorithm proceeds towards an optimized solution by randomly selecting a new solution that is near the current solution, and then comparing the two. If the cost function that is being minimized decreases with the new solution it is accepted and the algorithm can proceed to the next iteration. If, on the other hand, the cost function increases, the new solution is accepted with a probability:

$$\Pr = \exp\left(-\frac{\Delta CF}{T}\right) \quad [12]$$

where ΔCF is the change in the cost function, and T is the current unitless "temperature" of the system (if the cost function were a measure of the energy of the system, then unitless temperature would be replaced by kBT where kB is the Boltzmann constant and T is a temperature measured, for example, in Kelvin). For the simulations shown here a geometric temperature decrease was used so that the unitless temperature for an iteration i+1 was given by:

$$T_{i+1} = \alpha T_i \quad [13]$$

where Ti is the temperature in the previous iteration, and a is a constant with a value between 0 and 1. This constant was chosen to be 0.9998 to provide very slow cooling of the system.

Figure 5A:
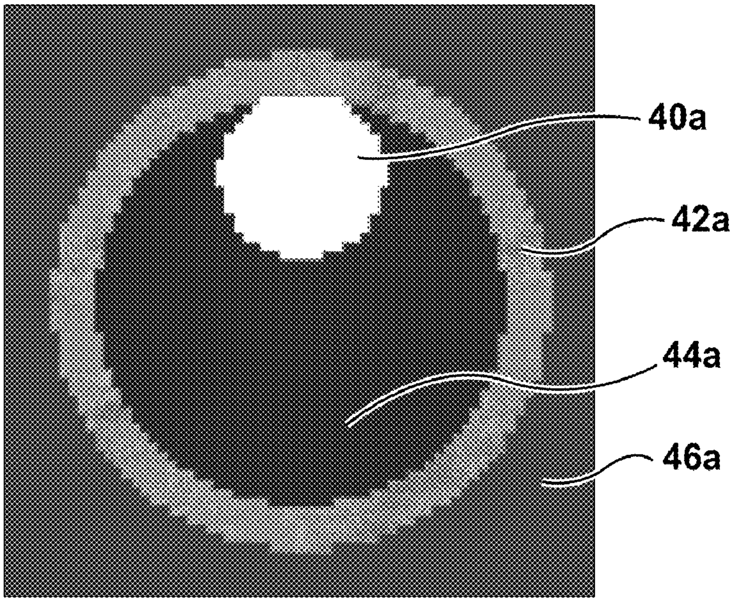
FIGS. 5*a* and 5*b* show two desired SNR images.

Two different examples of the desired SNR, $SNR_D$ are shown in FIGS. 5_a_ and 5_b_. Both figures have SNR values of 30, 15, 5, and 0. The SNR value of 30 is represented by the lightest nodule 40_a_ in the phantom and the SNR value of O is represented by the dark area 46_a_ outside the phantom. In FIG. 5_a_ the SNR was designed to be 15 at the skinline 42_a_ and 5 throughout the rest of the phantom, indicated at 44_a_. While in FIG. 5_b_ most of the phantom is defined as an SNR 15, indicated at 42_b_, with a region at the bottom of the phantom designed to be a region where less dose is desired, indicated at 44_b_. Both desired SNR images were used to determine optimal fluence patterns for the mathematical phantom. The matrices containing the desired SNR values were 65×65 pixels, and 180 projections were desired of the phantom, resulting in a modulation factor matrix of size 65×180 (a total of 11,700 values to be optimized). Using the symmetry of the SNR patterns optimized for the number of angles required to optimize the modulation factor over could be cut in half, reducing the problem to 5,850 values to be optimized. The initial value of the modulation factor was chosen to be one everywhere, which would be equivalent to imaging without any modulating filter placed in the beam. The cost function for iteration i was described by $$CF_i = \frac{\left(\sum_{x,y} (W_{SNR}(SNR_i - SNR_D))^2\right)}{\left(\sum_{x,y} (W_{SNR}(SNR_o - SNR_D))^2\right)} + w\frac{(D_i)}{(D_o)} \quad [14]$$

The matrix $W_{SNR}$ weighted the SNR difference in each pixel differently before the sum in each pixel was calculated. Although the dose across the image could be similarly weighted, in this case only the total dose absorbed by the phantom was used. The dose and totalled SNR difference were normalized by their initial values to facilitate comparison between the values. The value of w to weight the sum of the two normalized values was set at one to provide equal weighting between reducing dose and providing the desired SNR. This also results in a cost function with an initial value of two, as shown in FIG. 6.

Figure 6:
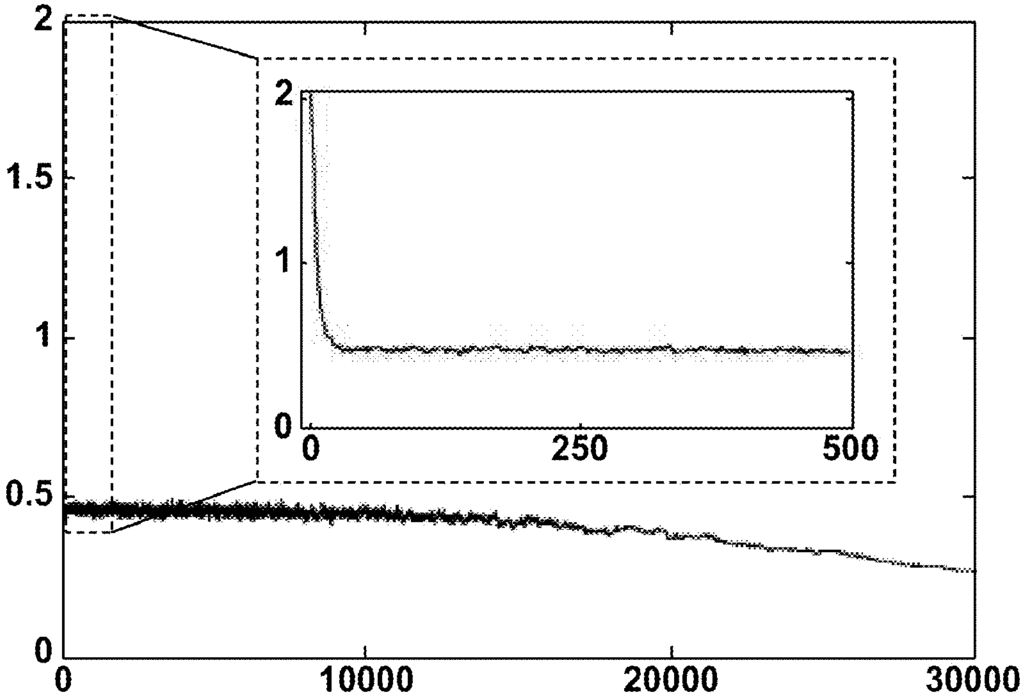
FIG. 6 shows a graph of a cost function.

As illustrated in FIG. 6 the cost functions tended to have an initial sharp decrease followed by a slow decrease. The cost function, which began with a value of two, was reduced to a value of 0.5 in approximately 20 iterations. This is because the initial modulation provided the highest dose possible. Beginning the optimization with a solution that is nearer to an optimized solution removes the sharp decrease at the beginning of the optimization process. Implementing OASCT could potentially use a small library of general modulation factors that are designed for certain anatomical regions. This would shorten the optimization process when performed for specific patients.

Figure 7:
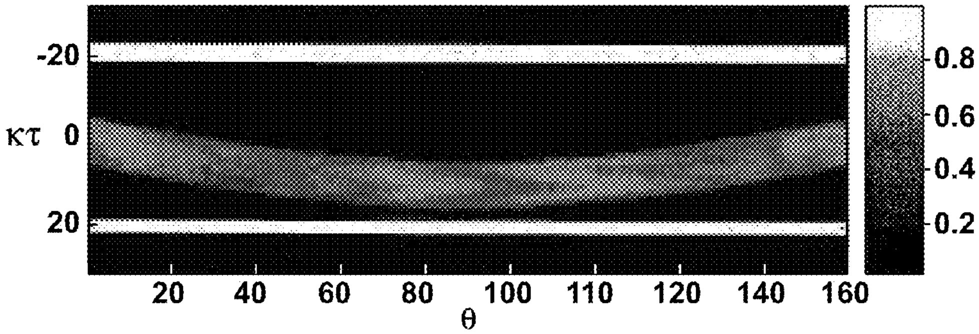
FIG. 7 shows a modulation function as a function of gantry angle and position.
Figure 8A:
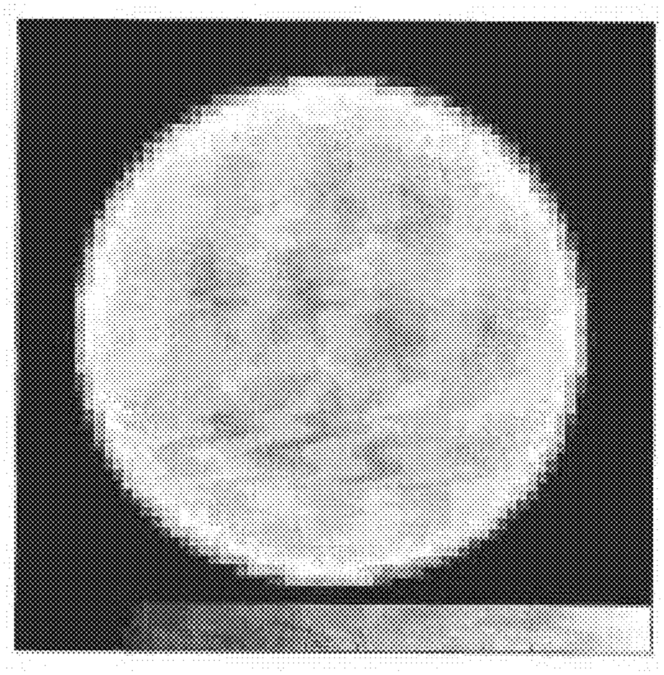
FIGS. 8*a*, 8*b*, 8*c* and 8*d* show, respectively, theoretical SNR with no modulation, SNR after optimization with uniform $W_{SNR}$, image acquired with no modulation, and image acquired using modulation pattern.
Figure 8B:
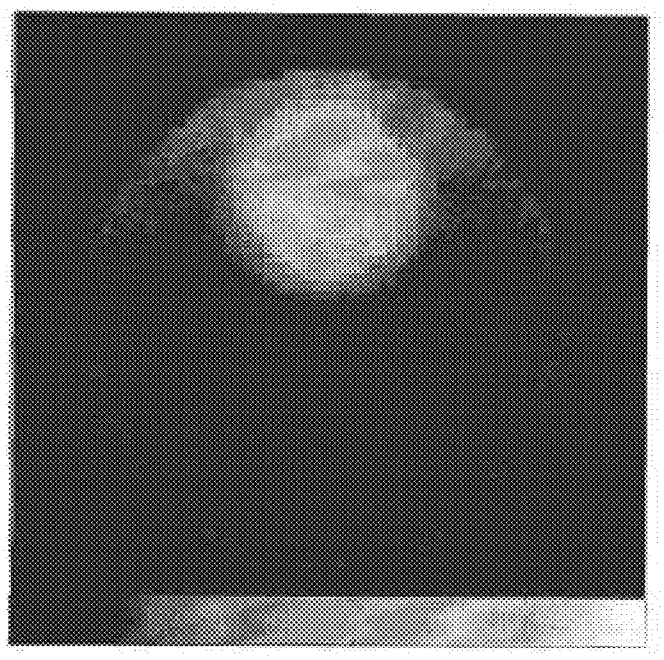
Figure 8C:
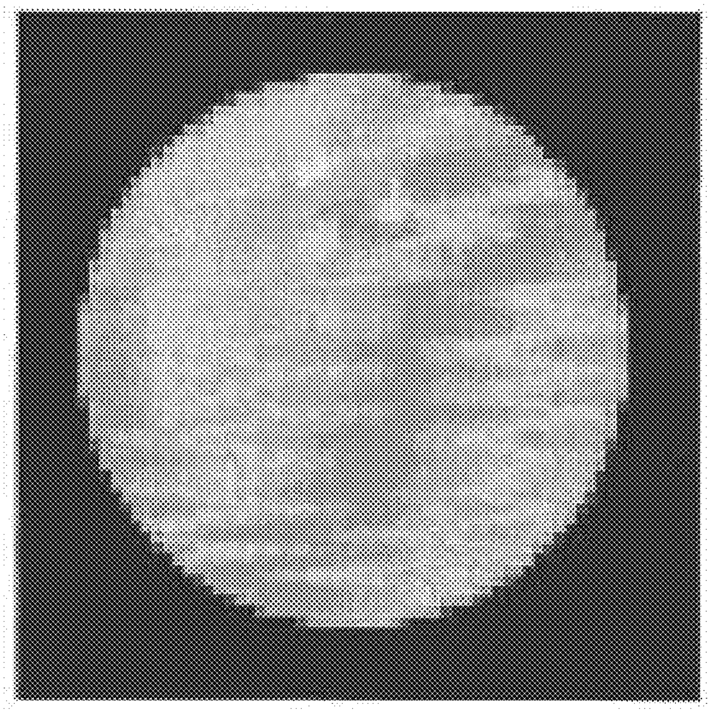
Figure 8D:
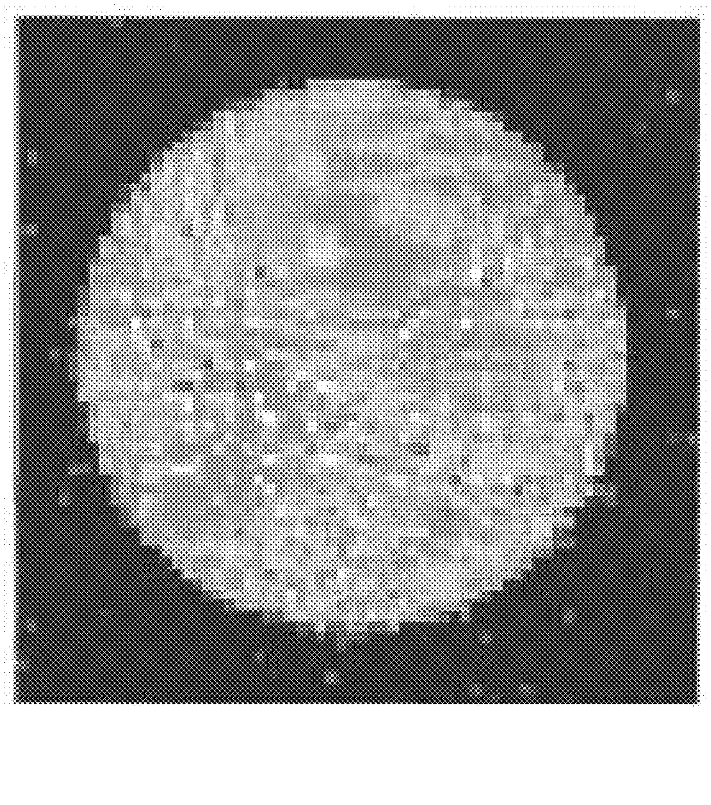

For the SNR distribution shown in FIG. 5_a_ the optimization process determined a value for $m_{\theta_i}(u,v)$ (FIG. 7) using equal weighting on all SNR values ($W_{SNR}$ equal to one). The right hand portion of FIG. 7 indicates a scale indicative of the value of the modulation function, $m_{\theta_i}(u,v)$ in the range [0,1]. The main portion of FIG. 7 shows the variation of the modulation function as a function of gantry angle, shown on the horizontal axis, and positioned across the image, shown along the vertical axis. As shown in FIG. 7, the value of $m_{\theta_i}(u,v)$ corresponding to where low SNR is desired had a value of approximately 0.04. For other positions, there is a band of higher value modulation function, which shifts following a sine waveform as shown in FIG. 7. Thus, at either side of FIG. 7, for gantry angles of 0 degrees and 180 degrees, this higher value modulation function is found at approximately kτ=0. It shifts downwards towards kτ=approx. 10, for the gantry angle 90 degrees. This is so that the desired SNR values will be achieved as closely as possible.

Applying this modulation gave images with distinct patterns of SNR (FIGS. 8_a_, 8_b_, 8_c_, 8_d_). FIG. 8_a_ illustrates the theoretical SNR in an unmodulated case. FIG. 8_b_ illustrates the SNR after the optimization process with uniform $W_{SNR}$. FIG. 8_c_ illustrates the image acquired with no modulation and FIG. 8_d_ illustrates the image acquired using the modulated pattern. The theoretical SNR shown is based on the evaluation of equations 5 and 6. The desired SNR was not achieved, likely because what was defined as the desired SNR was impossible to achieve given the constraints of the system. FIG. 8_b_ shows SNR values of approximately 19, 8.3, and 6.5 at the locations where the SNR was defined to be 30, 15, and 5. FIG. 8_a_, with no modulation applied, had an SNR of approximately 30 across the image. The relative doses in the unmodulated and modulated cases were 1 and 0.15 respectively. The CNR of the nodules was 6.6±1.2 in the unmodulated case, and decreased to 3.2±0.9 when modulation was applied. The cost function was decreased from 2 to 0.082.

If the weighting $W_{SNR}$ is changed on the SNR a different $m_{\theta_i}(u,v)$ will be found. Performing the same optimization, but changing $W_{SNR}$ to be 3 where the SNR is desired to be 30, and keeping it as 1 everywhere else, provides a optimization with higher dose, and less noise where we desire high SNR. FIG. 9_a_ shows the SNR distribution when $W_{SNR}$ is tripled and in this case the relative dose is increased to 0.21, the SNR (where it had a desired value of 30) was approximately 24, and the CNR of the nodules was 3.9±0.7. FIG. 9_b_ shows the image acquired when the $W_{SNR}$ is tripled in the region of higher SNR.

Figure 5B:
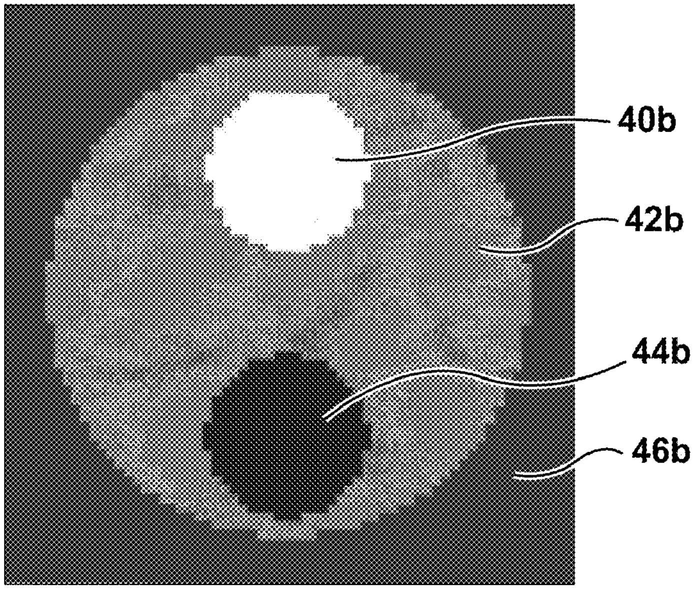
Figure 9A:
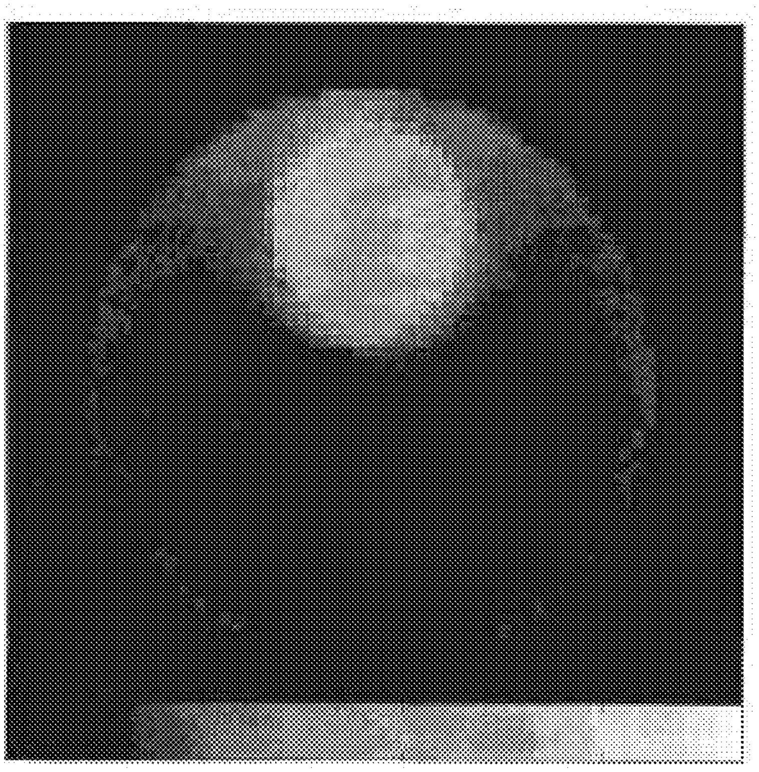
FIGS. 9*a* and 9*b* show, respectively, the SNR distribution and the image acquired with $W_{SNR}$ tripled in regions of higher SNR.
Figure 9B:
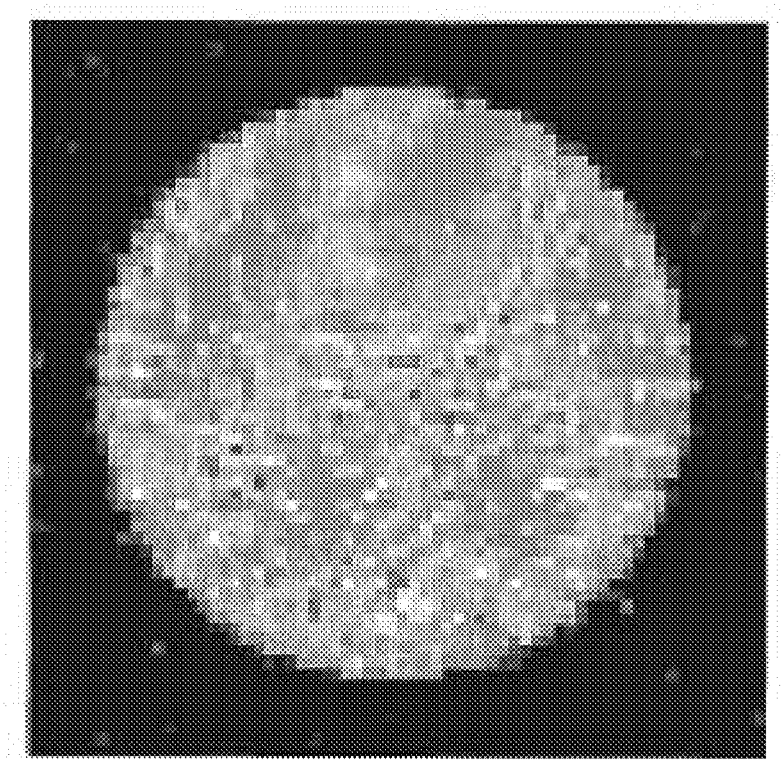
Figure 9C:
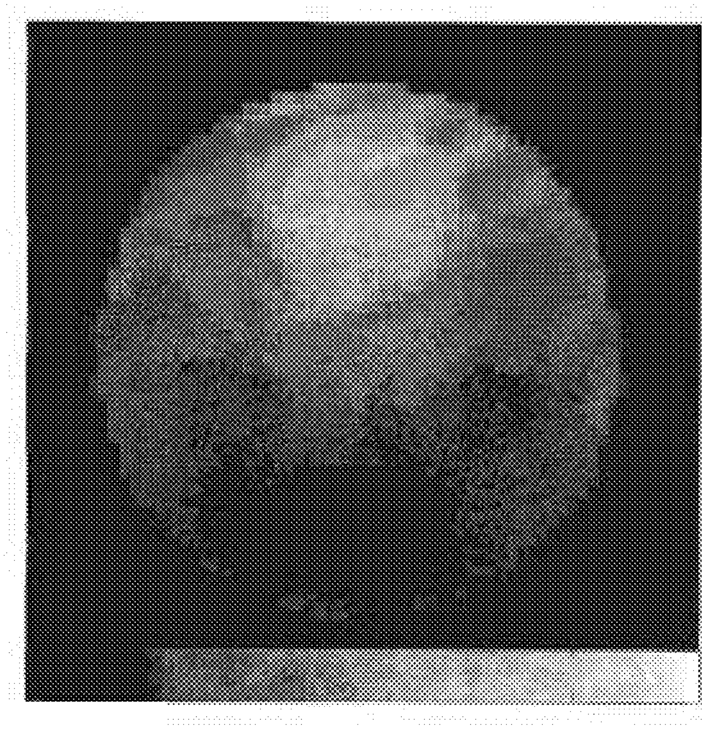
Figure 9D:
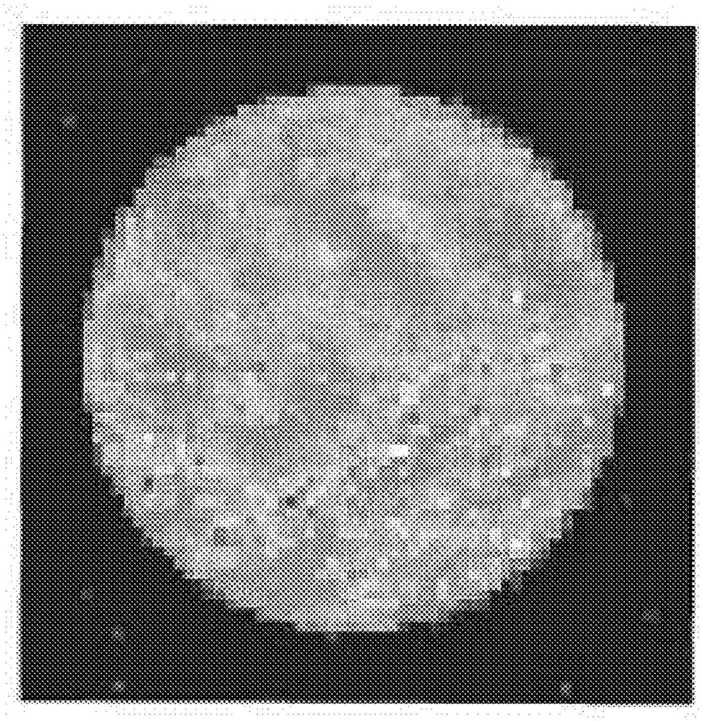

For the optimization using the SNR from FIG. 5_b_, $W_{SNR}$ was set at 3 for the areas where SNR was desired to be 30 and 5. $W_{SNR}$ was one where SNR was desired to be 15. FIG. 9_c_ shows the SNR distribution when $W_{SNR}$ is tripled and for this case the SNR achieved was approximately 21, 7.8, and 5.9 for the regions that were desired to be 30, 15, and 5. The relative dose was 0.18 and the CNR of the nodules was 3.7±0.7. FIG. 9*d* shows the image acquired when the $W_{SNR}$ is tripled for the desired SNR shown in FIG. 5*b*.

OASCT has the potential to greatly decrease dose to patients by concentrating image quality on desired regions of interest (ROIs). It will allow the prescription of desired image quality and dose throughout a volume, and an iterative optimization process will design patterns of modulation to be applied during imaging to acquire images as near as possible to those desired. This optimization process can account for numerous parameters of the imaging system, including the efficiency of the detector, the presence of x-ray scatter reaching the detector, and the constraints of the modulator used to form the intensity modulated fluence patterns. As mentioned above, there are various possibilities for constructing the modulator, using either a spatial or temporal compensating filter. For OASCT a spatial modulator would ideally be able to have a different optimized shape for each angle that a projection image is acquired at.

The simulation detailed above demonstrates the potential of this method, but more advanced work may be needed to be performed to determine how a real system may respond to the application of OASCT. The use of Monte Carlo methods (see G. Jarry, S. A. Graham, D. J. Moseley, et al. "Characterization of scattered radiation in kV CBCT images using Monte Carlo simulations," Med Phys. (submitted)) is a possibility for investigating OASCT. This would allow realistic modeling of OASCT, with the additional benefit of being able to choose which properties are included so that they may be studied individually (as opposed to experimental imaging CT measurements where it may be difficult to separate the causes and effects of different properties).

The mathematical formulation helps to demonstrate how modulation can be used to alter the noise in projections and reconstructed volumes. However, the formulas used are for parallel beam geometry, but the OASCT imaging system can be implemented for any number of imaging geometries, source-detector trajectories, or reconstruction algorithms. Also left out of the formulation are quantities such as the x-ray scatter reaching the detector and the energy dependence of the x-rays used for imaging. Although these omissions may affect the results in equations 5 and 6 it is expected that modulated fluence patterns still have the ability to provide the desired optimized images. The optimization process to determine the modulated fluence patterns will be a mathematical optimization rather than an exact inversion so that equations similar to 5 and 6 are not necessary to implement OASCT.

Reference will now be made to FIG. 10 and details of a louvre compensator. This compensator comprises two sets of louvres 110, 112 extending perpendicularly to one another and overlapping so that rotation of individual louvres may be used to select a desired opening. The louvres are formed from a material that absorbs substantially all the x-rays incident on them, so that the effective x-ray beam is the opening in the louvre compensator.

Figure 10B:
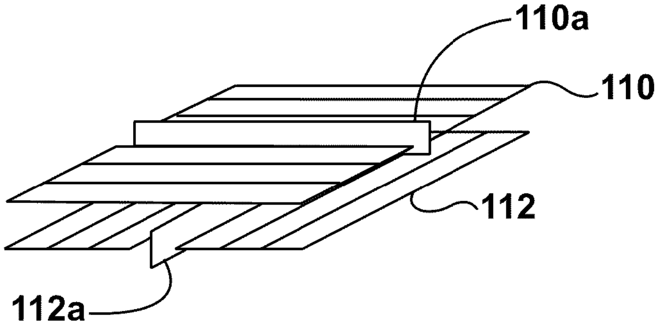
FIG. 10*b* shows the louvre compensation of FIG. 10*a* in a partial open position.

FIG. 10*b* shows one simple opening scheme where one louvre 110*a* in the first set of louvres and another louvre 110*b* in the second set are both rotated through 90 degrees so as, in effect to provide two open slots running perpendicularly to one another. The individual louvres 110*a*, 110*b* will be located in the middle of these slots but their dimensions are such that they will have no significant effect on the x-ray beam as it passes through each slot thus formed.

Figure 10C:
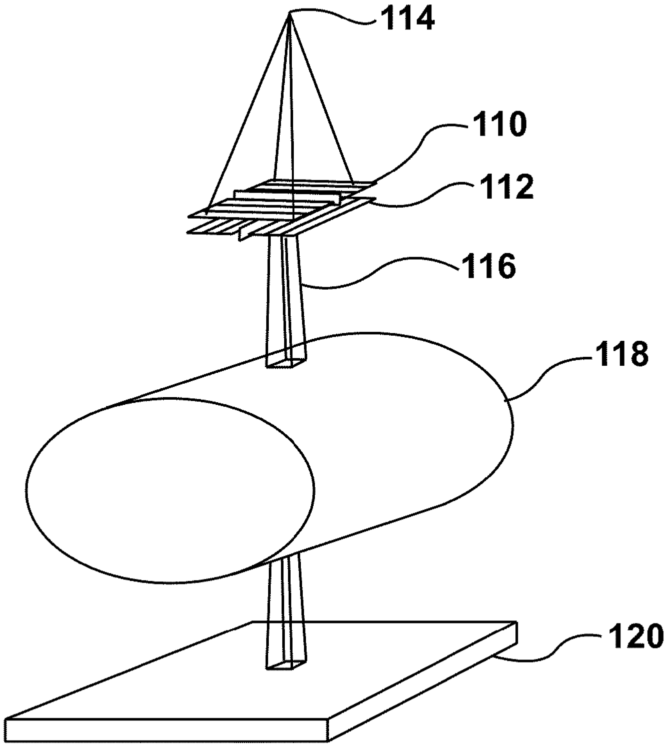
FIG. 10*c* shows the louvre compensation of FIGS. 10*a*, *b* in use.

As indicated in FIG. 10*c*, an x-ray beam originates as a cone-beam from source 114 and is instant on the louvre compensator 110, 112. Due to the open configurations of the individual louvres 110*a*, 112*a*, an approximately square aperture is provided, that permits an x-ray beam 116 of square, conical shape to extend towards and through a body indicated schematically at 118. The beam passes through the body and is detected at a detector.

Figure 11A:
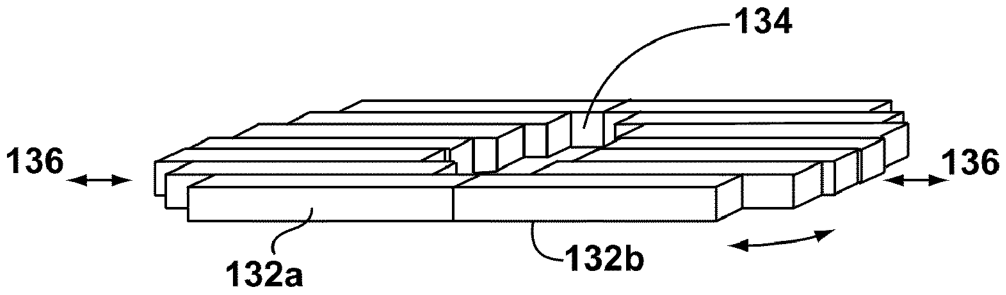
FIG. 11*a* shows an example of another temporal compensation scheme, comprising a multi-leaf compensator.

Referring to FIG. 11*a*, this shows an alternative compensator scheme, with a compensator indicated schematically at 130. Here, the compensator 130 includes a plurality of individual pairs of elements indicated for one pair 132*a*, 132*b*. These elements 132*a*, 132*b* are movable in and out from a central plane as indicated by the arrows 136, so as to define the shape and area of an aperture 134.

Figure 11B:
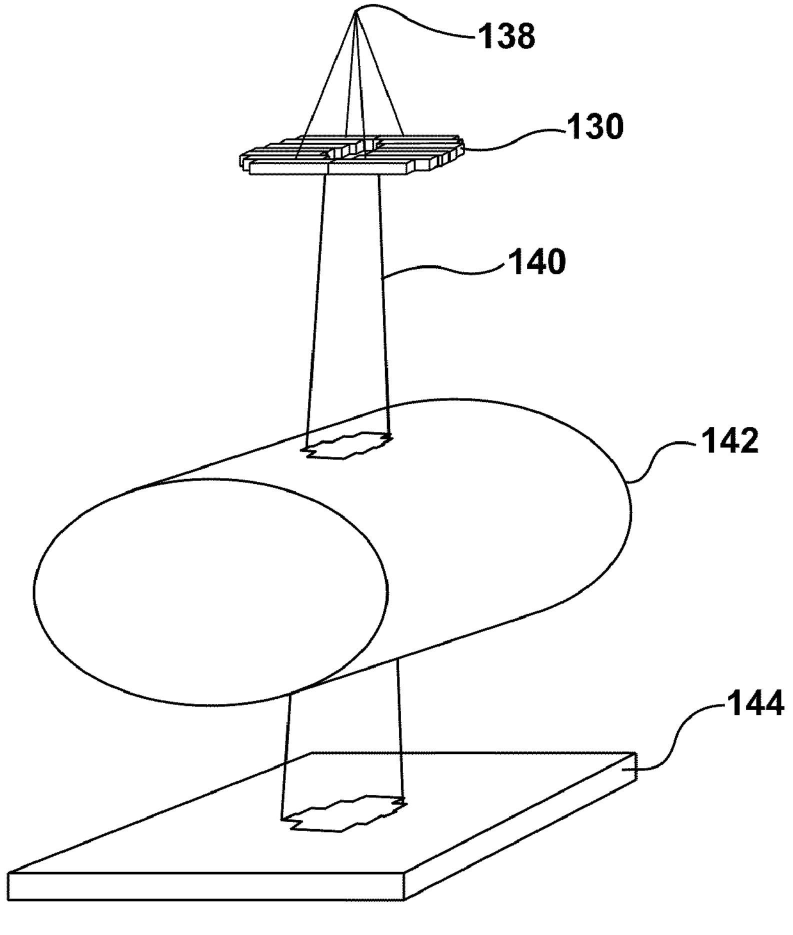
FIG. 11*b* shoes the multi-leaf compensation of FIG. 11*a* in use.

Referring to FIG. 11*b*, with a selected aperture 134 set for the compensator 130, an x-ray source 138 is then arranged, to pass a beam through the aperture 134. This generates a beam of the desired shape as indicated at 140. The shaped beam 140 then passes through a body indicated schematically at 142, to impinge on a detector 144.

It will be understood that, either instead of or as well as, the temporal modulators shown in FIGS. 10 and 11, one or more spatial moderators can be used. A spatial moderator will provide some fixed modulation, and may result in some beam hardening.

Accordingly, it is shown that it is possible to design an imaging CT system with gantry angle dependent compensation, capable of achieving desired image quality in defined ROIs and distributions.

While the above description provides examples of one or more processes or apparatuses, it will be appreciated that other processes or apparatuses may be within the scope of the accompanying claims.

The invention claimed is:

1. An imaging system, the system comprising:

an electromagnetic radiation source for directing a beam at an object to be imaged;

a modulator placed between the radiation source and the object to be imaged; and a computer for performing calculations based on a desired distribution of image quality to determine a pattern of fluence to be applied by the modulator, wherein the modulator comprises a plurality of individual elements, each being substantially impervious to radiation and being movable between an open position and a closed position, wherein open positions of the individual elements define an aperture permitting passage of the beam from the radiation source, wherein the modulator is configured as a louvre compensator comprising a first set of substantially parallel louvres extending in one direction and a second set of substantially parallel louvres extending in another direction and overlapping the first set, and wherein, by selected positioning of at least one louvre of the first set in the open position and at least one louvre of the second set in the open position, an aperture is defined for passage of the beam from the radiation source to the object.

2. The imaging system of claim 1, wherein the directions of the two sets of louvres extend generally perpendicularly to one another.

3. The imaging system of claim 2, wherein, due to the open positions of the at least one louvre of the first set and the at least one louvre of the second set, the aperture is approximately square and permits a modulated beam of generally square, conical shape to extend towards the object.

4. A method of operating imaging computed tomography using an electromagnetic radiation source and a plurality of detectors to generate an image of an object, the method comprising:

defining a region of interest for the object;

defining desired image characteristics for the region of interest;

performing calculations to determine a pattern of fluence to be applied by the radiation source to generate the desired image characteristics; and modulating the radiation source to generate the pattern of fluence, wherein the step of performing calculations comprises optimizing image characteristics and patient dose iteratively according to:

$$\min\{\|C(\vec{r})-C_i(\vec{r})\|+w\|D(\vec{r})-D_i(\vec{r})\|\},$$

where $\vec{r}$ represents positions of voxels in a reconstructed image of the object, $C(\vec{r})$ is an image metric of the reconstructed image of the object defining the desired image characteristics and $C_i(\vec{r})$ is $C(\vec{r})$ in the ith step, $D(\vec{r})$ is the patient dose in the object being imaged and $D_i(\vec{r})$ is $D(\vec{r})$ in the ith step, $\|(C(\vec{r})$ represents optimal image quality, $\|D(\vec{r})-D_i(\vec{r})\|$ represents optimal patient dose, and w is weighting given to the dose, and wherein the step of performing calculations comprises weighting of image characteristics and patient dose across individual voxels according to:

$$\min\{\|W_c(\vec{r})(C(\vec{r})-C_i(\vec{r}))\|+w\|W_D(\vec{r})(D(\vec{r})-D_i(\vec{r}))\|\},$$

where $W_C$ and $W_D$ are a matrix of weights of image quality and patient dose, respectively.

5. The method of claim 4, wherein the desired image characteristics comprise at least one of desired levels of contrast-to-noise ratio (CNR) and signal-to-noise ratio (SNR).

6. The method of claim 4, wherein the desired image characteristics provide at least one of: desired image quality in at least one defined region of interest;

and at least one desired distribution of an image quality.

7. The method of claim 4, wherein the step of performing calculations comprises solving an inverse problem using an iterative solution.

8. The method of claim 7, wherein the step of performing calculations comprises:

i) solving the inverse problem according to the equation:

$$m(u,v)I(u,v)=G^{-1}[C(\vec{r})],$$

where v=v(z) and u=u(x,y), x, y and z are dimensions of the object being imaged, I(u,v) represents intensity of the radiation applied to the object from the radiation source, m(u,v) represents modulation of the radiation by the object, and $G^{-1}$ is an operator which relates the image metric $C(\vec{r})$ to the applied radiation intensities; and ii) iteratively solving the equation:

$$\min\{\|C(\vec{r})-C_i(\vec{r})\|\},$$

where, for each step i, the image metric $C_i(\vec{r})$ is calculated and compared to the desired quantity $C(\vec{r})$.

9. The method of claim 8, wherein the step of performing calculations comprises constraining lower and upper bounds on the image metric, so that in the reconstructed image:

$$\underline{C}(\vec{r})\leq\hat{f}(\vec{r})\leq\overline{C}(\vec{r}),$$

where $\hat{f}(\vec{r})$ represents the reconstructed image of the object, and $\underline{C}(\vec{r})$ and $\overline{C}(\vec{r})$ are lower and upper bounds, respectively, of the desired $C(\vec{r})$ at each point $\vec{r}$.

10. The method of claim 7, wherein the calculations being performed comprise considering at least one of:

the dependence of image quality on primary fluence transiting through the object;

the dependence on scatter fluence to the detector;

the dependence upon scattered dose to the object and its dependence on $\phi(\theta,u,v)$, where θ represents an angle at which the radiation is applied to the object from the radiation source; and the exposure dependent detective quantum efficiency (DQE) of the detector DQE ($\phi(\theta,u,v)$).

11. The method of claim 4, comprising providing temporal modulation of the radiation source.

12. The method of claim 4, comprising providing spatial modulation of the radiation source.

13. The method of claim 4, comprising both spatial and temporal modulation of the radiation source.

14. The method of claim 4, comprising providing a temporal modulator comprising a plurality of individual elements adapted to absorb radiation, and moving these elements to provide desired temporal modulation.

15. The method of claim 4, wherein the region of interest is defined from at least one of: previously acquired patient images; and a library of population models.

* * * * *

UNITED STATES PATENT AND TRADEMARK OFFICE
CERTIFICATE OF CORRECTION

PATENT NO. : 8,406,373 B2
APPLICATION NO. : 13/209731
DATED : March 26, 2013
INVENTOR(S) : Sean A. Graham et al.

It is certified that error appears in the above-identified patent and that said Letters Patent is hereby corrected as shown below:

In the Specification:

1. Column 6, line 29, "$\hat{f}(\vec{r})$" should read -- $C(\vec{r})$ --;

2. Column 6, line 30, "$\underline{C}(\vec{r}) \leq \hat{f}(\vec{r}) \leq \overline{C}(\vec{r})$" should read -- $\underline{C}(\vec{r}) \leq C(\vec{r}) \leq \overline{C}(\vec{r})$--;

In the Claims:

3. Column 13, line 29, "$\|(C(\vec{r})$" should read -- $\|C(\vec{r}) - C_i(\vec{r})\|$ --;

4. Column 14, line 6, "intensity" should read --fluence--;

5. Column 14, line 21, "$\underline{C}(\vec{r}) \leq \hat{f}(\vec{r}) \leq \overline{C}(\vec{r}),$" should read -- $\underline{C}(\vec{r}) \leq C(\vec{r}) \leq \overline{C}(\vec{r}),$ --; and 6. Column 14, line 22, "$\hat{f}(\vec{r})$" should read -- $C(\vec{r})$ --.

Signed and Sealed this
Twenty-second Day of October, 2013

Teresa Stanek Rea
*Deputy Director of the United States Patent and Trademark Office*